(12) United States Patent
Gupta et al.

(10) Patent No.: US 7,575,909 B2
(45) Date of Patent: Aug. 18, 2009

(54) **OXIDOREDUCTASE FROM *PICHIA CAPSULATA***

(75) Inventors: Antje Gupta, Wiesbaden (DE); Anke Tschentscher, Eltville (DE); Maria Bobkova, Idstein (DE)

(73) Assignee: IEP GmbH (DE)

( * ) Notice: Subject to any disclaimer, the term of this patent is extended or adjusted under 35 U.S.C. 154(b) by 0 days.

(21) Appl. No.: 10/561,043

(22) PCT Filed: May 28, 2004

(86) PCT No.: PCT/EP2004/005831

§ 371 (c)(1),
(2), (4) Date: Dec. 12, 2006

(87) PCT Pub. No.: WO2004/111083

PCT Pub. Date: Dec. 23, 2004

(65) Prior Publication Data

US 2007/0243594 A1 Oct. 18, 2007

(30) Foreign Application Priority Data

Jun. 18, 2003 (DE) ................................ 103 27 454

(51) Int. Cl.
*C12N 9/02* (2006.01)
*C12P 7/42* (2006.01)

(52) U.S. Cl. ...................... 435/189; 435/146

(58) Field of Classification Search ................ None
See application file for complete search history.

(56) References Cited

U.S. PATENT DOCUMENTS

| 6,312,933 B1 | 11/2001 | Kimoto et al. |
| 7,220,564 B2 | 5/2007 | Kizaki et al. |
| 7,232,672 B2 | 6/2007 | Weiner et al. |
| 7,332,312 B2 | 2/2008 | Kizaki et al. |
| 7,335,757 B2 | 2/2008 | Hiraoka et al. |

FOREIGN PATENT DOCUMENTS

| WO | 93/18138 | 9/1993 |
| WO | 02/086126 | 10/2002 |

OTHER PUBLICATIONS

Jones; "Horse Liver Alcohol Dehydrogenase An Illustrative Example Of The Potential Of Enzymes In Organic Synthesis"; Chiba, I., S. Fukui and L. B. Wingard, Jr. (Ed.) . Enzyme Engineering, vol. 6. International Conference, Kashikojima, Japan, Sep. 20-25, 1981; XXII+538P. Plenum Press: New York, N.Y., USA; London England, Illus Series: Enzyme E 1982, , pp. 107-116; XP009039464.
Xie et al; "NAD$^+$-Dependent (S)-Specific Secondary Alcohol Dehydrogenase Involved In Stereoinversion of 3-Pentyn-2-ol Catalyzed by *Nacordia fusca* AKU 2123"; Bioscience Biothecnology and Biochemistry, Bd., 63, Nr. 10, pp. 1721-1729; Oct. 1999; XP009039491.
Schütte et al; "Purification and Characterization Of A Nicotinamide Adenine Dinucleotide-dependent Secondary Alcohol Dehydrogenase From *Candida boidinii*"; Biochemica et Biophysica Acto. Jun. 16, 1982, Bd. 716, Nr. 3, pp. 298-307; XP001203741.
Cannino et al; "The Alcohol Dehydrogenase Gene: Distribution Among Sulfolobales and Regulation in *Sulfolobus solfataricus*"; FEMS Microbiology Letters, Bd. 170, Nr. 1, pp. 31-39; Jan. 1, 1999; XP02304730.
Bayer et al; "Purification and Characterization of The NADH-dependent (S)-specific 3-oxobutyryl-CoA Reductase From *Clostridium tyrobutycricym*"; Archive of Microbiology, Bd. 163, Nr. 4, pp. 310-312; 1995; XP009039585.
Sambrook, Joseph and David W. Russell, "Molecular Cloning, A Laboratory Manual", Protocol 32, Third Edition, vol. 1, Cold Spring Harbor Laboratory Press, Cold Spring Harbor, NY, 2001, pp. 1.138-1.142, www.molecularcloning.com.

*Primary Examiner*—Nashaat T. Nashed
*Assistant Examiner*—Mohammad Younus Meah
(74) *Attorney, Agent, or Firm*—Lowe Hauptman Ham & Berner, LLP

(57) ABSTRACT

The invention relates to a NADH-dependent oxidoreductase obtained from yeasts, for example, of the genus *Pichia*, more particularly from *Pichia capsulata*. The oxidoreductace used in an enzymatic process for enantioselective reduction of organic ketocompounds to the corresponding (S)-hydroxy compounds and in an enzymatic process for an antioselective preparation of (S)-hydroxy compounds in a two phase system using the isolated, recombinantly overexpressed oxidoreductacse from *Pichia capsulata*.

7 Claims, No Drawings

SEQUENCE LISTING

<160> NUMBER OF SEQ ID NOS: 10

<210> SEQ ID NO 1
<211> LENGTH: 1175
<212> TYPE: DNA
<213> ORGANISM: Pichia capsulata

<400> SEQUENCE: 1

```
cgcggtggcg gccgctctag aactagtgga tcccccgggc tgcaggaatt cggcacgagg      60
atctttctca actacaatgt ctgctctctc caaaacccag gccggttaca tcttcaagaa     120
gggtgccggt cacatcgtca aggccgaggt tccaatcccc aagccaactg gtgcccaatc     180
tcttcttagg gtcaaggctg caggaatgtg ccactctgac ttgcacgtca ttggagaaac     240
attggaggtc cctaccgatg ggtacgtgct cggtcacgaa attgctggtg aattggtgga     300
gatcggagac tcggtcaacc ctgaagtttt taaggtggga ggccgttatg ctgttcatgg     360
actgaattcg tgtggatcct gtgagatgtg tcgtaccggt catgacaatg actgtactgg     420
aaatgaatcg aaatggtacg gtctgggaat tagtggtggt taccagcagt acctgctggt     480
gccaaattcg caccatctat tgcctattcc agataacgtg tcctacgaag ttgctgctgc     540
cacctctgat gctgtcttga ctccatacca tgctatcaag aattccggag tgactccatc     600
ttctaaggtg ttgatgtttg gtctgggtgg tttgggatcg aacgcacttc agatcctcaa     660
ggcatttgga gcctatgtgg ttgccgttga tgtcaagccc gcatccaaag caattgccga     720
cgaattcaaa gcggatgaat tctataccga tatcagccaa tcttcttgga aaccagcctc     780
gtttgattac tgttttgact tcgtttcgct gcaggtcacc ttcgacatct gccagaagta     840
tatcaagtcc cacggtacca tcttcccagt gggtctgggc tcgagcaagc tgactttcga     900
cttgggaaac ctggcattgc gtgaagtaaa aattgttggt aacttctggg gtacttctca     960
ggaacagatc gaagcaatgg agctggttag ctcgggtagg gtcaagcctc aagttcacac    1020
caccgaactt gaaaaccttc ctgaatcact tgaaaaactg gaggagggta agatcaatgg    1080
aagattggtt atgcttccat gatcacaaac tatttataac gagatacgag aaaaagttta    1140
atatgatgtc gttttccaa tcaaaagggg ggccc                                1175
```

<210> SEQ ID NO 2
<211> LENGTH: 366
<212> TYPE: PRT
<213> ORGANISM: Artificial Sequence
<220> FEATURE:
<223> OTHER INFORMATION: Description of Artificial Sequence: Synthetic
      Protein

<400> SEQUENCE: 2

```
Ala Val Ala Ala Ala Leu Glu Leu Val Asp Pro Pro Gly Cys Arg Asn
  1               5                  10                  15

Ser Ala Arg Gly Ser Phe Ser Thr Thr Met Ser Ala Leu Ser Lys Thr
             20                  25                  30

Gln Ala Gly Tyr Ile Phe Lys Lys Gly Ala Gly His Ile Val Lys Ala
         35                  40                  45

Glu Val Pro Ile Pro Lys Pro Thr Gly Ala Gln Ser Leu Leu Arg Val
     50                  55                  60

Lys Ala Ala Gly Met Cys His Ser Asp Leu His Val Ile Gly Glu Thr
 65                  70                  75                  80

Leu Glu Val Pro Thr Asp Gly Tyr Val Leu Gly His Glu Ile Ala Gly
```

```
                85                  90                  95
Glu Leu Val Glu Ile Gly Asp Ser Val Asn Pro Glu Val Phe Lys Val
            100                 105                 110
Gly Gly Arg Tyr Ala Val His Gly Leu Asn Ser Cys Gly Ser Cys Glu
            115                 120                 125
Met Cys Arg Thr Gly His Asp Asn Asp Cys Thr Gly Asn Glu Ser Lys
            130                 135                 140
Trp Tyr Gly Leu Gly Ile Ser Gly Gly Tyr Gln Gln Tyr Leu Leu Val
145                 150                 155                 160
Pro Asn Ser His His Leu Leu Pro Ile Pro Asp Asn Val Ser Tyr Glu
                165                 170                 175
Val Ala Ala Thr Ser Asp Ala Val Leu Thr Pro Tyr His Ala Ile
            180                 185                 190
Lys Asn Ser Gly Val Thr Pro Ser Ser Lys Val Leu Met Phe Gly Leu
            195                 200                 205
Gly Gly Leu Gly Ser Asn Ala Leu Gln Ile Leu Lys Ala Phe Gly Ala
            210                 215                 220
Tyr Val Ala Val Asp Val Lys Pro Ala Ser Lys Ala Ile Ala Asp
225                 230                 235                 240
Glu Phe Lys Ala Asp Glu Phe Tyr Thr Asp Ile Ser Gln Ser Ser Trp
                245                 250                 255
Lys Pro Ala Ser Phe Asp Tyr Cys Phe Asp Phe Val Ser Leu Gln Val
            260                 265                 270
Thr Phe Asp Ile Cys Gln Lys Tyr Ile Lys Ser His Gly Thr Ile Phe
            275                 280                 285
Pro Val Gly Leu Gly Ser Ser Lys Leu Thr Phe Asp Leu Gly Asn Leu
290                 295                 300
Ala Leu Arg Glu Val Lys Ile Val Gly Asn Phe Trp Gly Thr Ser Gln
305                 310                 315                 320
Glu Gln Ile Glu Ala Met Glu Leu Val Ser Ser Gly Arg Val Lys Pro
                325                 330                 335
Gln Val His Thr Thr Glu Leu Glu Asn Leu Pro Glu Ser Leu Glu Lys
            340                 345                 350
Leu Glu Glu Gly Lys Ile Asn Gly Arg Leu Val Met Leu Pro
            355                 360                 365

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 3
gtaatacgac tataggg                                              17

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 4
caattaaccc tcactaaagg g                                         21
```

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 5
ggaattccat atgtctgctc tctccaaaac                                        30

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 6
cactgcatgc tgatgtctgc tctctccaaa ac                                     32

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 7
cccaagcttt catggaagca taaccaatct t                                      31

<210> SEQ ID NO 8
<211> LENGTH: 1026
<212> TYPE: DNA
<213> ORGANISM: Pichia capsulata

<400> SEQUENCE: 8
atgtctgctc tctccaaaac ccaggccggt tacatcttca agaagggtgc cggtcacatc        60
gtcaaggccg aggttccaat ccccaagcca actggtgccc aatctcttct tagggtcaag       120
gctgcaggaa tgtgccactc tgacttgcac gtcattggag aaacattgga ggtccctacc       180
gatgggtacg tgctcggtca cgaaattgct ggtgaattgg tggagatcgg agactcggtc       240
aaccctgaag tttttaaggt gggaggccgt tatgctgttc atggactgaa ttcgtgtgga       300
tcctgtgaga tgtgtcgtac cggtcatgac aatgactgta ctggaaatga atcgaaatgg       360
tacggtctgg gaattagtgg tggttaccag cagtacctgc tggtgccaaa ttcgcaccat       420
ctattgccta ttccagataa cgtgtcctac gaagttgctg ctgccacctc tgatgctgtc       480
ttgactccat accatgctat caagaattcc ggagtgactc catcttctaa ggtgttgatg       540
tttggtctgg gtggtttggg atcgaacgca cttcagatcc tcaaggcatt tggagcctat       600
gtggttgccg ttgatgtcaa gcccgcatcc aaagcaattg ccgacgaatt caaagcggat       660
gaattctata ccgatatcag ccaatcttct tggaaaccag cctcgtttga ttactgtttt       720
gacttcgttt cgctgcaggt caccttcgac atctgccaga agtatatcaa gtcccacggt       780
accatcttcc cagtgggtct gggctcgagc aagctgactt cgacttggg aaacctggca       840 ttgcgtgaag taaaaattgt tggtaacttc tggggtactt ctcaggaaca gatcgaagca       900
atggagctgg ttagctcggg tagggtcaag cctcaagttc acaccaccga acttgaaaac       960

```
cttcctgaat cacttgaaaa actggaggag ggtaagatca atggaagatt ggttatgctt    1020
ccatga                                                                1026
```

<210> SEQ ID NO 9
<211> LENGTH: 341
<212> TYPE: PRT
<213> ORGANISM: Pichia capsulata

<400> SEQUENCE: 9

```
Met Ser Ala Leu Ser Lys Thr Gln Ala Gly Tyr Ile Phe Lys Lys Gly
  1               5                  10                  15

Ala Gly His Ile Val Lys Ala Glu Val Pro Ile Pro Lys Pro Thr Gly
             20                  25                  30

Ala Gln Ser Leu Leu Arg Val Lys Ala Gly Met Cys His Ser Asp
         35                  40                  45

Leu His Val Ile Gly Glu Thr Leu Glu Val Pro Thr Asp Gly Tyr Val
     50                  55                  60

Leu Gly His Glu Ile Ala Gly Glu Leu Val Glu Ile Gly Asp Ser Val
 65                  70                  75                  80

Asn Pro Glu Val Phe Lys Val Gly Arg Tyr Ala Val His Gly Leu
                 85                  90                  95

Asn Ser Cys Gly Ser Cys Glu Met Cys Arg Thr Gly His Asp Asn Asp
            100                 105                 110

Cys Thr Gly Asn Glu Ser Lys Trp Tyr Gly Leu Gly Ile Ser Gly Gly
        115                 120                 125

Tyr Gln Gln Tyr Leu Leu Val Pro Asn Ser His His Leu Leu Pro Ile
    130                 135                 140

Pro Asp Asn Val Ser Tyr Glu Val Ala Ala Thr Ser Asp Ala Val
145                 150                 155                 160

Leu Thr Pro Tyr His Ala Ile Lys Asn Ser Gly Val Thr Pro Ser Ser
                165                 170                 175

Lys Val Leu Met Phe Gly Leu Gly Gly Leu Gly Ser Asn Ala Leu Gln
            180                 185                 190

Ile Leu Lys Ala Phe Gly Ala Tyr Val Val Ala Val Asp Val Lys Pro
        195                 200                 205

Ala Ser Lys Ala Ile Ala Asp Glu Phe Lys Ala Asp Glu Phe Tyr Thr
    210                 215                 220

Asp Ile Ser Gln Ser Ser Trp Lys Pro Ala Ser Phe Asp Tyr Cys Phe
225                 230                 235                 240

Asp Phe Val Ser Leu Gln Val Thr Phe Asp Ile Cys Gln Lys Tyr Ile
                245                 250                 255

Lys Ser His Gly Thr Ile Phe Pro Val Gly Leu Gly Ser Ser Lys Leu
            260                 265                 270

Thr Phe Asp Leu Gly Asn Leu Ala Leu Arg Glu Val Lys Ile Val Gly
        275                 280                 285

Asn Phe Trp Gly Thr Ser Gln Glu Gln Ile Glu Ala Met Glu Leu Val
    290                 295                 300

Ser Ser Gly Arg Val Lys Pro Gln Val His Thr Thr Glu Leu Glu Asn
305                 310                 315                 320

Leu Pro Glu Ser Leu Glu Lys Leu Glu Glu Gly Lys Ile Asn Gly Arg
                325                 330                 335

Leu Val Met Leu Pro
            340
```

```
<210> SEQ ID NO 10
<211> LENGTH: 12
<212> TYPE: PRT
<213> ORGANISM: Pichia capsulata

<400> SEQUENCE: 10

Lys Thr Gln Ala Gly Tyr Ile Phe Lys Lys Gly Ala
 1               5                  10
```

OXIDOREDUCTASE FROM *PICHIA CAPSULATA*

CROSS-REFERENCE TO RELATED APPLICATIONS

The present Application is based on International Application No. PCT/EP2004/005831, filed May 28, 2004, which in turn corresponds to DE 103 27 454.5-41 filed on Jun. 18, 2003, and priority is hereby claimed under 35 USC §119 based on these applications. Each of these applications are hereby incorporated by reference in their entirety into the present application.

The present invention relates to an oxidoreductase, to a process for the enantioselective reduction of carbonyl compounds to the corresponding (S)-hydroxy compounds and to a process for obtaining the chiral (R)-hydroxy compound.

Optically active hydroxy compounds are valuable chiral components with broad applicability for the synthesis of pharmacologically active compounds, aromatic substances, pheromones, agricultural chemicals or enzyme inhibitors.

At the same time, the number of carbonyl reductases which are suitable for large-scale applications in biocatalysis and are available at low cost in sufficient amounts is extremely limited. The following NADH-dependent S-specific carbonyl reductases are known:

Alcohol dehydrogenase from horse liver (HLADH) (Enzyme Engineering, Vol 6, 1982, page 107),
Alcohol dehydrogenase from yeast (YADH) (Alcohol dehydrogenases: The Enzymes (1963), pages 25-83. New York: Academic Press),
Carbonyl reductase from *Candida parapsilosis* (CPCR) (U.S. Pat. No. 5,523,223 and U.S. Pat. No. 5,763,236),
Carbonyl reductase from *Rhodococcus erythropolis* (RECR) (U.S. Pat. No. 5,523,223) and *Norcardia fusca* (Biosci. Biotechnol. Biochem., 63 (10) (1999), pages 1721-1729),
Alcohol dehydrogenase from *Candida boidinii* (Biochim., Biophys. Acta 716, (1982), pages 298-307) or
Alcohol dehydrogenase from *Sulfolobus solfataricus* (FEMS Microbiology Letters, 170 (1999), pages 31-39).

None of the above-mentioned carbonyl reductases has so far been employed on a large scale. The main reason therefor, besides substrate spectra which often are too narrow or the low enantioselectivity of the enzymes, is above all the availability of said enzymes. So far it has not been possible to provide most of the above-mentioned enzymes in sufficient amounts and at low cost.

Another problem arising in the application of the above-mentioned carbonyl reductases is the regeneration of the cofactors NADH or NADPH. The known processes employ either a substrate-coupled coenzyme regeneration, for example with 2-propanol, or an enzyme-coupled coenzyme regeneration, for example with formate dehydrogenase.

A disadvantage of the enzyme-coupled coenzyme regeneration with formate dehydrogenase is the low specific activity thereof (4 to 10 U/mg), therefore, even the recombinant formate dehydrogenase is comparatively expensive (J. Biotechnol. Bioeng. [1999] 64, pages 187-193).

A disadvantage of the substrate-coupled coenzyme regeneration with isopropanol is the unfavourable equilibrium position and the insufficient enzyme stability towards the cosubstrates used such as isopropanol.

It is the object of the invention to provide an oxidoreductase which is characterized by a broad substrate spectrum, high enantioselectivity and high stability towards organic solvents.

Said object is achieved by an oxidoreductase in such a way that it reduces a carbonyl compound to the corresponding (S)-hydroxy compound in the presence of NADH and water.

It has now been found that the above-mentioned disadvantages of the prior art processes can be obviated by means of a new oxidoreductase.

The invention suitably relates to oxidoreductases which are obtainable from yeasts of the genuses *Pichia* or *Candida*, in particular from *Pichia capsulata*.

In a further embodiment, the invention relates to oxidoreductase from *Pichia capsulata* which has the DNA-sequence according to SEQ ID NO: 8 and the amino acid sequence according to SEQ ID NO: 9. These sequences are described in the attached sequence listing.

In one embodiment, the invention relates to oxidoreductase in which more than 70% of the amino acids is identical to the amino acid sequence SEQ ID NO: 9 and which has a specific activity of more than 1 μmol per mg protein, based on the reaction of ethyl-4-chloro-3-oxobutanoate to (R)-ethyl-4-chloro-3-hydroxybutanoate. An oxidoreductase is preferred in which 80% to 99.5%, in particular 90% to 99.5%, especially 99% to 99.5%, are amino acids identical to the amino acid sequence of SEQ ID NO: 9. Measuring the specific activity of oxidoreductase according to SEQ ID NO: 9 or of the derivatives or the analogon thereof, as defined below, is carried out by means of the test system described in Example 1.

The oxidoreductase according to the invention is characterized in that it exhibits an additional amount of 1 to 40 amino acids or 1 to 40 amino acids less than the oxidoreductase having the amino acid sequence SEQ ID NO: 9 and that it has a specific activity of more than 1 μmol per mg protein, based on the reaction of ethyl-4-chloro-3-oxobutanoate to (R)-ethyl-4-chloro-3-hydroxybutanoate. Oxidoreductases are preferred in which 1 to 25 amino acids, in particular 2 to 20 amino acids, or preferably 3 to 10 amino acids, more or less than in the amino acid sequence of SEQ ID NO: 9 are present.

Furthermore, the invention relates to the oxidoreductase which has the amino acid sequence of SEQ ID NO: 9 and is modified once, twice, three, four or five times by a water-soluble polymer and in which the specific activity amounts to more than 1 μmol per mg protein, based on the reaction of ethyl-4-chloro-3-oxobutanoate to (R)-ethyl-4-chloro-3-hydroxybutanoate. A water-soluble polymer is polyethylene glycol, for example. The binding of the polyethylene glycol preferably takes place at the N-terminal end of the protein according to SEQ ID NO: 9. The oxidoreductase according to SEQ ID NO: 9 can also be bound to a solid body such as polyethylene, polystyrene, polysaccharide, cellulose or cellulose derivatives.

Furthermore, the invention relates to a protein fragment representing fragments of the amino acid sequence SEQ ID NO: 9, having a number of 5 to 30 amino acids per fragment. Fragments of SEQ ID NO: 9 are preferred, having a chain length of 6 to 25 amino acids, in particular 8 to 20 amino acids or 10 to 18 amino acids, in particular of the amino acid sequence SEQ ID NO: 10. Said fragments may, for example, be used for discovering the oxidoreductase according to the invention from *Pichia capsulata* or from any other microorganism.

Furthermore, the invention relates to a fusion protein which is characterized in that it represents the oxidoreductase having the amino acid sequence SEQ ID NO: 9 or fragments of the amino acid sequence SEQ ID NO: 9, having a number of 5 to 30 amino acids which are connected via a peptide bond to a further polypeptide at the N-terminal or carboxy-terminal end. Fusion proteins can, for example, be separated more easily from other proteins or are expressed in the cells in larger amounts.

Furthermore, the invention relates to an antibody which binds specifically to the oxidoreductase according to SEQ ID NO: 9 or SEQ ID NO: 10. The production of said antibodies is carried out according to known methods by immunizing suitable mammals and subsequently obtaining the antibodies. The antibodies can be monoclonal or polyclonal.

The invention also relates to the isolated nucleic acid sequence which codes for the oxidoreductase according to SEQ ID NO: 9 and SEQ ID NO: 10.

Furthermore, the invention relates to an isolated DNA-sequence of the oxidoreductase which catalyzes the reduction of a carbonyl compound to the corresponding (S)-hydroxy compounds in the presence of NADH and water, wherein the DNA-sequence is selected from the group a) DNA-sequence which has the nucleotide sequence according to SEQ ID NO: 8, SEQ ID NO: 5, SEQ ID NO: 6 or SEQ ID NO: 7, or the respective complementary strand,
b) DNA-sequence which hybridizes to one or several of the DNA-sequences according to a) or to the complementary strands thereof, with the hybridization taking place unter stringent conditions, and
c) DNA-sequence which, as a result of the degeneration of the genetic code, encodes a protein which is encoded by one or several of the DNA-sequences according to a) or b).

The conditions prevailing during hybridization are described in Sambrok and Russel, Molecular Cloning a Laboratory Manual, Vol 1, Chapter 1, Protocol 30-32.

Furthermore, the invention relates to a DNA-sequence in which more than 70% of the nucleic acid bases is identical to the DNA-sequence according to SEQ ID NO: 8 or to the complementary strands thereof and which encodes the oxidoreductase which has a specific activity of more than 1 µmol per mg protein, based on the reaction of ethyl-4-chloro-3-oxobutanoate to (R)-ethyl-4-chloro-3-hydroxybutanoate. DNA-sequences are preferred in which 80% to 99.5%, in particular 90% to 99.5%, especially 99% to 99.5%, of the nucleic acid bases is identical to the DNA-sequence according to SEQ ID NO: 8.

Furthermore, the invention relates to a nucleic acid sequence having 10 to 50 nucleic acid bases which has a sequence corresponding to a part or several parts of the DNA-sequence according to SEQ ID NO: 8 or to the complementary strands thereof. A nucleic acid sequence having 15 to 45 nucleic acid bases, in particular 20 to 40 bases or 30 to 40 nucleic acid bases of the above-mentioned DNA-sequences, is preferred. The above-mentioned nucleic acid sequences are suitable as molecular probes or as primers for the polymerase-chain reaction (PCR).

Furthermore, the invention relates to a cloning vector comprising one or several of the above-mentioned nucleic acid or DNA sequences. Furthermore, the invention relates to an expression vector located in a bacterial, insect, plant or mammalian cell and comprising one or several of the above-mentioned nucleic acid or DNA sequences which are linked in an appropriate manner to an expression control sequence. Furthermore, the invention relates to a host cell which is a bacterial, yeast, insect, plant or mammalian cell and has been transformed or transfected with an expression vector.

The identities of the previously mentioned DNA-sequences or of the previously mentioned amino acid sequence are calculated by adding up the number of amino acids or nucleic acid bases which are identical to partial sequences of the respective proteins or DNA-sequences and by dividing the sum by the total number of amino acids or nucleic acid bases and multiplying the same by one hundred.

Suitable cloning vectors are, for example, ppCR-Script, pCMV-Script, pBluescript (Stratagene), pDrive cloning vector (Quiagen, Hilden, Germany), pS Blue, pET Blue, pET LIC-vectors (Novagen, Madison, USA) as well as TA-PCR cloning vectors (Invitrogen, Karlsruhe, Germany).

Suitable expression vectors are, for example, pKK223-3, pTrc99a, pUC, pTZ, pSK, pBluescript, pGEM, pQE, pET, PHUB, pPLc, pKC30, pRM1/pRM9, pTrxFus, pAS1, pGEx, pMAL or pTrx.

Suitable expression control sequences are, for example, trp-lac (tac)-promotor, trp-lac (trc) promotor, lac-promotor, T7-promotor or λpL-promotor.

The oxidoreductase from *Pichia capsulata* is a homotetramer having a molecular weight of 34±2 kDa, determined in an SDS-gel, and a molecular weight of 140±10 kDa, determined via gel permeation chromatography. The optimum temperature of oxidoreductase ranges from 40° C. to 45° C., the optimum pH for the reduction reaction is from 6.5 to 7.0, and the optimum pH for the oxidation reaction is from 7.8 to 8.2. The oxidoreductase from *Pichia capsulata* exhibits good temperature and pH stabilities and is stable for 5 hours within a pH range of 5.5 to 8.5 and in a temperature range of 15° C. to 40° C. and, furthermore, exhibits high stability in organic solvents.

The enzyme can be isolated especially from yeasts of the genus *Pichia* and can be detected in a spectrophotometric test via a decrease in NADH at 340 nm in the presence of an appropriate substrate, for example ethyl-4-chloro-3-oxobutyrate or 2-butanone.

The oxidoreductase according to the invention from *Pichia capsulata* was cloned and could be overexpressed in *Escherichia coli* (*E. coli*) with activities of from 1.000 to 10.000 U/g *E. coli* wet weight. The enzyme is inexpensive and available in large amounts. Sequence comparisons in databases show that the oxidoreductase according to the invention from *Pichia capsulata* is a zinc-dependent carbonyl reductase.

The invention also relates to a process for obtaining oxidoreductase from *Pichia capsulata*. For this purpose, the DNA which codes for the oxidoreductase from *Pichia capsulata* is expressed, for example, in a suitable prokaryotic or eukaryotic microorganism. Preferably, the oxidoreductase from *Pichia capsulata* is transformed into an *E. coli* strain and expressed in particular in *E. coli* BL21star (DE3) cells.

The oxidoreductase from *Pichia capsulata* can, for example, be obtained such that the above-mentioned recombinant *E. coli* cells are cultivated, the expression of oxidoreductase is induced and subsequently, after about 10 to 18 hours (h), the cells are digested by ultrasonic treatment or wet grinding with glass beads in a globe mill (Retsch GmbH, Haan, Germany, 10 min, 24 Hz). The cell extract obtained can either be used directly or purified further. For this purpose, the cell extract is centrifuged, for example, and the supernatant obtained is subjected to ion exchange chromatography, for instance, by ion exchange chromatography in a Q-Sepharose Fast Flow® device (Pharmacia).

Furthermore, the invention relates to a process for the enantioselective reduction of carbonyl compounds to the corresponding (S)-hydroxy compounds, which process is characterized in that a) a carbonyl compound is reduced to the corresponding (S)-hydroxy compound in the presence of the oxidoreductase according to one or several of claims 1 to 9, NADH and water, and b) the chiral (S)-hydroxy compound formed is isolated.

The process according to the invention has a high service life, an enantiomeric purity of more than 95% of the chiral (S)-hydroxy compounds produced and a high yield based on the amount of carbonyl compound that is fed.

By the term "NADH", reduced nicotinamide adenine dinucleotide is understood.

By the term "NAD", nicotinamide adenine dinucleotide is understood.

By the term "carbonyl compound", compounds of Formula I $$R1\text{-}C(O)\text{—}R2 \qquad (I)$$

are understood, for example.

The moiety R1 is, e.g.,
1) $—(C_1\text{-}C_{20})$-alkyl, wherein alkyl is linear-chain or branched,
2) $—(C_2\text{-}C_{20})$-alkenyl, wherein alkenyl is linear-chain or branched and contains one, two, three or four double bonds, depending on the chain length,
3) $—(C_2\text{-}C_{20})$-alkynyl, wherein alkynyl is linear-chain or branched and optionally contains one, two, three or four triple bonds,
4) $—(C_6\text{-}C_{14})$-aryl,
5) $—(C_1\text{-}C_8)$-alkyl-$(C_6\text{-}C_{14})$-aryl,
6) $—(C_5\text{-}C_{14})$-heterocycle which is unsubstituted or substituted one to three times by halogen, hydroxyl, amino or nitro, or
7) $—(C_3\text{-}C_7)$-cycloalkyl,
wherein the moieties mentioned under 1) to 7) are unsubstituted or substituted one, two or three times, independently of each other, by
a) —OH,
b) halogen such as fluorine, chlorine, bromine or iodine,
c) —NO$_2$ or
d) —NH$_2$.

The moiety R2 is, e.g.,
1) $—(C_1\text{-}C_6)$-alkyl, wherein alkyl is linear-chain or branched,
2) $—(C_2\text{-}C_6)$-alkenyl, wherein alkenyl is linear-chain or branched and contains one, two or three double bonds, depending on the chain length,
3) $—(C_2\text{-}C_6)$-alkynyl, wherein alkynyl is linear-chain or branched and optionally contains one or two triple bonds, or
4) $—(C_0\text{-}C_{10})$-alkyl-C(O)—O—$(C_1\text{-}C_6)$-alkyl, wherein alkyl is linear or branched and is unsubstituted or substituted one to three times by halogen, hydroxyl, amino or nitro,
wherein the moieties mentioned under 1) to 4) are unsubstituted or substituted one, two or three times, independently of each other, by
a) —OH,
b) halogen such as fluorine, chlorine, bromine or iodine,
c) —NO$_2$ or
d) —NH$_2$.

By the term chiral "(S)-hydroxy compound", compounds of Formula II $$R1\text{-}C(OH)\text{—}R2 \qquad (II).$$

are understood, for example, wherein the —OH-group is usually positioned in an (S)-configuration relative to the carbon atom to which it is bound and R1 and R2 have the same meaning as in Formula I.

If, however, a carbonyl group or a halogen atom is located close to the alcohol, the nomenclature changes and the enantioselective alcohols are then also referred to as (R)-alcohols. This, however, is merely a matter of nomenclature and does not alter the stereoselective way of how the oxidoreductase according to the invention carries out the reduction.

By the term "aryl", aromatic carbon moieties comprising 6 to 14 carbon atoms within the ring are understood. $—(C_6\text{-}C_{14})$ aryl moieties are, for instance, phenyl, naphthyl, 1-naphthyl, 2-naphthyl, biphenylyl, 2-biphenylyl, 3-biphenylyl and 4-biphenylyl, anthryl or fluorenyl. Biphenylyl moieties, naphthyl moieties and in particular phenyl moieties are preferred aryl moieties. By the term "halogen", an element from the family of fluorine, chlorine, bromine and iodine is understood. By the term "$—(C_1\text{-}C_{20})$ alkyl", a hydrocarbon moiety is understood the carbon chain of which is linear-chain or branched and comprises 1 to 20 carbon atoms, for example, methyl, ethyl, propyl, isopropyl, butyl, tertiary butyl, pentyl, hexyl, heptyl, octyl, nonenyl or decanyl. By the term "—C$_0$ alkyl", a covalent bond is understood.

By the term "$—(C_3\text{-}C_7)$ cycloalkyl", cyclic hydrocarbon moieties such as cyclopropyl, cyclobutyl, cyclopentyl, cyclohexyl or cycloheptyl are understood.

The term "$—(C_5\text{-}C_{14})$ heterocycle" stands for a monocyclic or bicyclic 5-membered to 14-membered heterocyclic ring which is partially or completely saturated. N, O and S are examples of heteroatoms. Moieties derived from pyrrole, furan, thiophene, imidazole, pyrazole, oxazole, isoxazole, thiazole, isothiazole, tetrazole, 1,2,3,5-oxathiadiazole-2-oxide, triazolone, oxadiazolone, isoxazolone, oxadiazolidinedione, triazole substituted by F, —CN, —CF$_3$ or —C(O)—O—(C$_1$-C$_4$) alkyl, 3-hydroxypyrro-2,4-dione, 5-oxo-1,2,4-thiadiazole, pyridine, pyrazine, pyrimidine, indole, isoindole, indazole, phthalazine, quinoline, isoquinoline, quinoxaline, quinazoline, cinnoline, carboline- and benz-anellated, cyclopenta-, cyclohexa- or cyclohepta-anellated derivatives of said heterocycles are examples of the terms "$—(C_5\text{-}C_{14})$ heterocycle". The moieties 2- or 3-pyrrolyl, phenylpyrrolyl such as 4- or 5-phenyl-2-pyrrolyl, 2-furyl, 2-thienyl, 4-imidazolyl, methylimidazolyl, e.g. 1-methyl-2-, -4- or -5-imidazolyl, 1,3-thiazole-2-yl, 2-pyridyl, 3-pyridyl, 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, e.g. 1-methyl, 5-methyl, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzo-thienyl, 2-benzoxazolyl or benzothiazolyl or dihydropyrinidyl, pyrrolidinyl, e.g. 2- or 3-(N-methylpyrrolidinyl), piperazinyl, morpholinyl, thiomorpholinyl, tetrahydrothienyl or benzodioxolanyl are particularly preferred.

Preferred compounds of Formula I are, for example, ethyl-4-chloroacetoacetate, methylacetoacetate, ethyl-8-chloro-6-oxooctanoate, ethyl-3-oxovaleriate, 4-hydroxy-2-butanone, ethyl-2-oxovaleriate, ethyl-2-oxo-4-phenylbutanoate, ethyl pyruvate, ethyl phenyl glyoxylate, 1-phenyl-2-propanone, 2,3-dichloroacetophenone, acetophenone, 2-octanone, 3-octanone or 2-butanone.

The S-alcohols formed correspondingly are, for example, (R)-ethyl-4-chloro-3-hydroxybutanoate, ethyl-(S)-2-hydroxy-4-phenylbutanoate, (S)-2-octanol or (R)-ethyl-8-chloro-6-hydroxyoctanoate.

Suitable oxidoreductases come, for instance, from *Pichia capsulata*. In the process according to the invention, the oxidoreductase can be used either in a completely purified or in a partially purified state. The process is carried out with the oxidoreductase according to the invention or with cells containing the oxidoreductase according to the invention. In doing so, the cells used can be provided in a native, permeabilized or lysed state. Preferably, the cloned oxidoreductase according to SEQ ID NO: 9 is used.

The volume activity of the employed oxidoreductase is from 100 units/ml (U/ml) to 5,000 U/ml, preferably to about 500 U/ml.

5,000 to 2,000,000 U of oxidoreductase, preferably about 10,000-200,000 U, are used per kg of compound of Formula I to be reacted. Thereby, the enzyme unit 1 U corresponds to the enzyme amount which is required for reacting 1 µmol of the compound of Formula I per minute (min).

Furthermore, the invention relates to a process for the enantioselective reduction of carbonyl compounds to the corresponding (S)-hydroxy compounds, wherein
a) a carbonyl compound is reduced to the corresponding (S)-hydroxy compound in the presence of the oxidoreductase according to the invention, NADH and water,
b) the NAD formed by the oxidoreductase is reduced to NADH with a cosubstrate, and
c) the chiral (S)-hydroxy compound formed is isolated.

The amounts of carbonyl compounds and oxidoreductases which are used are equal to the above-mentioned amounts in the described processes. Suitable cosubstrates for the process according to the invention are alcohols such as ethanol, 2-propanol (isopropanol), 2-butanol, 2-pentanol or 2-octanol. These cosubstrates are reacted to the corresponding ketones and NADH by the oxidoreductase according to the invention and NAD. Thereby, NADH is regenerated.

The amount of cosubstrate for the regeneration of NAD to NADH such as isopropanol is from 5% to 50%, based on the total volume, preferably from 8% to 20%, in particular from 10% to 15%.

Furthermore, the invention relates to a process for the enantioselective recovery of (S)-hydroxy compounds, wherein
a) a carbonyl compound is reduced to the corresponding (S)-hydroxy compound in the presence of the oxidoreductase according to the invention, NADH and water,
b) the NAD formed by the oxidoreductase is reduced to NADH with a dehydrogenase and a cosubstrate, and
c) the chiral (S)-hydroxy compound formed is isolated.

Suitable dehydrogenases are, for example, NADH-dependent alcohol dehydrogenases from baker's yeast, from *Candida boidinii* or *Candida parapsilosis*. Suitable cosubstrates for the alcohol dehydrogenase used are alcohols such as ethanol, 2-propanol (isopropanol), 2-butanol, 2-pentanol or 2-octanol.

Furthermore, the NAD reduction can also be carried out by means of formate dehydrogenase (Tishkov et al., J. Biotechnol. Bioeng. [1999] 64, 187-193, Pilot-scale production and isolation of recombinant NAD and NADP specific formate dehydrogenase). Suitable cosubstrates of formate dehydrogenase are, for example, salts of formic acid such as ammonium formate, sodium formate or calcium formate.

The substrate-coupled coenzyme regeneration is preferably used with a secondary alcohol such as ethanol, 2-propanol (isopropanol), 2-butanol, 2-pentanol or 2-octanol. Therefore, the process is preferably carried out without an additional dehydrogenase.

Preferably, a buffer, e.g. a potassium phosphate, tris/HCl or triethanolamine buffer having a pH value of 5 to 10, preferably a pH value of 6 to 9, is added to the water used in the process. The buffer concentration is from 10 mM to 150 mM.

In addition, the buffer can contain ions for stabilizing or activating the enzymes, for example zinc ions or magnesium ions.

The temperature is, for example, from 10° C. to 60° C., preferably from 30° C. to 55° C.

Furthermore, the invention relates to a process for the enantioselective recovery of (S)-hydroxy compounds, wherein
a) a carbonyl compound is reduced to the corresponding (S)-hydroxy compound in the presence of the oxidoreductase, NADH and water,
b) the reactions are carried out in the presence of an organic solvent, and
c) the chiral (S)-hydroxy compound formed is isolated.

The preferred organic solvents are, for example, diethyl ether, tertiary butyl methyl ether, diisopropyl ether, dibutyl ether, butyl acetate, heptane, hexane or cyclohexane.

If additional solvents are used, the reaction batch consists of an aqueous phase and an organic phase. The organic phase is formed by a suitable solvent in which the substrate is present in a dissolved state or by the water-insoluble substrate itself.

The organic phase makes up 5% to 80% of the total reaction volume, preferably 10% to 40%.

In the two-phase system according to the invention, the water forms one liquid phase, and the organic solvent forms the second liquid phase. In addition, a solid or another liquid phase can optionally be provided which results, for example, from oxidoreductase which has not been dissolved completely and/or from added enzymes or from the carbonyl compound. However, two liquid phases without a solid phase are preferred. Preferably, the two liquid phases are mixed mechanically so that large surfaces are formed between the two liquid phases.

The concentration of the cofactor NADH, based on the aqueous phase, is from 0.01 mM to 1 mM, in particular from 0.05 mM to 0.2 mM.

In the process according to the invention, the carbonyl compound is used in an amount of from 3% to 30%, based on the total volume, preferably of from 5% to 15%, in particular of 10%.

Furthermore, the invention relates to a process for the enantioselective reduction of carbonyl compounds to the corresponding (S)-hydroxy compounds, wherein
a) a carbonyl compound is reduced to the corresponding (S)-hydroxy compound in the presence of the oxidoreductase, NADH and water,
b) the reactions are carried out in the presence of an organic solvent,
c) the NAD formed by the oxidoreductase is reduced to NADH with a cosubstrate, and
d) the chiral (S)-hydroxy compound formed is isolated.

The amounts of carbonyl compounds and oxidoreductases that are used correspond to the above-mentioned processes. Suitable cosubstrates for the process are alcohols such as ethanol, 2-propanol (isopropanol), 2-butanol, 2-pentanol or 2-octanol. These cosubstrates are reacted to the corresponding ketones and NADH by the oxidoreductase and NAD. Thereby, NADH is regenerated.

The amount of cosubstrate such as isopropanol for the regeneration of NAD to NADH is from 5% to 50%, based on the total volume, preferably from 8% to 20%, in particular from 10% to 15%.

Furthermore, the invention relates to a process for the enantioselective reduction of carbonyl compounds to the corresponding (S)-hydroxy compounds, wherein
a) a carbonyl compound is reduced to the corresponding (S)-hydroxy compound in the presence of the oxidoreductase, NADH and water, b) the NAD formed by the oxidoreductase is simultaneously reduced to NADH with a dehydrogenase and a cosubstrate,
c) the reactions are carried out in the presence of an organic solvent, and
d) the chiral (S)-hydroxy compound formed is isolated.

Preferably, a further stabilizer for the alcohol dehydrogenase is used in the process according to the invention. Suitable stabilizers are, for example, glycerol, sorbitol, 1,4-DL-dithiothreitol (DTT) or dimethyl sulfoxide (DMSO).

The process according to the invention is carried out, for example, in a closed reaction vessel made of glass or metal. For this purpose, the components are transferred individually into the reaction vessel and stirred under an atmosphere of, e.g., nitrogen or air. Depending on the substrate and the carbonyl compound used, the reaction time amounts to from 1 hour to 48 hours, in particular from 2 hours to 24 hours.

Subsequently, the reaction mixture is reprocessed. For this purpose, the aqueous phase is separated and the organic phase is filtered. Optionally, the aqueous phase can be extracted once again and can be reprocessed further like the organic phase. Afterwards, the solvent is optionally evaporated from the filtered organic phase. In this way, the product (R)-ethyl-4-chloro-3-hydroxybutanoate is obtained with an enantiomeric purity of more than 99% and substantially free from the educt ethyl-4-chloroacetoacetate. After the distillation of the product, the total yield of the process amounts to 50% to 95%, based on the amount of educt that is used.

Furthermore, the invention relates to a process for the recovery of chiral (R)-hydroxy compounds of Formula II,

R1-C(OH)—R2    (II)

comprising the moieties R1 and R2 as previously defined. In said process,
a) a mixture containing the racemic compound of Formula II is incubated with the oxidoreductase according to the invention, NAD and water, and
b) the remaining chiral (R)-hydroxy compound of Formula II is isolated.

Thereby, the (S)-hydroxy compound of Formula II is reacted to the corresponding ketonic compound and NADH.

Furthermore, the invention relates to a process for the recovery of chiral (R)-hydroxy compounds of Formula II, wherein
a) a mixture containing the racemic compound of Formula II is incubated with the oxidoreductase according to the invention, NAD and water,
b) the NADH formed by the oxidoreductase is oxidized to NAD with a cosubstrate, and
c) the remaining chiral (R)-hydroxy compound of Formula II is isolated.

Furthermore, the invention relates to a process for the recovery of chiral (R)-hydroxy compounds of Formula II, wherein
a) a mixture containing the racemic compound of Formula II is incubated with the oxidoreductase according to the invention, NAD and water,
b) the NADH formed by the oxidoreductase is oxidized to NAD with a dehydrogenase and a cosubstrate, and
c) the remaining chiral (R)-hydroxy compound of Formula II is isolated.

In another embodiment, the invention relates to a process for the recovery of chiral (R)-hydroxy compounds of Formula II, wherein
a) a mixture containing the racemic compound of Formula II is incubated with the oxidoreductase according to the invention, NAD and water,
b) the reactions are carried out in the presence of an organic solvent, and
c) the remaining chiral (R)-hydroxy compound of Formula II is isolated.

A further process according to the invention for the recovery of chiral (R)-hydroxy compounds of Formula II is characterized in that
a) a mixture containing the racemic compound of Formula II is incubated with the oxidoreductase according to the invention, NAD and water,
b) the reactions are carried out in the presence of an organic solvent,
c) the NADH formed by the oxidoreductase is oxidized to NAD with a dehydrogenase and a cosubstrate, and
d) the remaining chiral (R)-hydroxy compound of Formula II is isolated.

The reaction conditions are basically the same as in the previously mentioned process for the enantiospecific reduction of the ketonic compounds of Formula I. However, instead of an enantioselective reduction of the ketonic compound of Formula I from the racemic mixture of the compound of Formula II, only the (S)-hydroxy compound of Formula II is oxidized enantioselectively to the corresponding ketonic compound. Thus, the (R)-hydroxy compound of Formula II remains and can be isolated.

Furthermore, instead of the alcohols used as cosubstrates such as ethanol, 2-propanol (isopropanol), 2-butanol, 2-pentanol or 2-octanol, the corresponding ketones thereof such as acetone are used in the process for a regeneration of the NAD. The acetone and NADH are, for example, reacted to NAD and isopropanol with the oxidoreductase according to the invention or an additional dehydrogenase. The amounts of ketone that are used are from 5% to 50%, based on the total volume, preferably from 8% to 20% and in particular from 10% to 15%.

In the following, the invention is illustrated by way of examples.

EXAMPLES

Example 1

Screening of Yeasts for S-specific Alcohol Dehydrogenase

For screening, a number of different yeast strains were cultivated in the following medium (all data in g/l): yeast extract (3), malt extract (3), peptone (5) and glucose (10). The medium was sterilized at 121° C. and the yeasts were cultivated without further pH-adjustment at 25° C. and on a shaker at 160 revolutions per minute (rpm). Subsequently, 125 mg of cells were resuspended with 800 µl of digestion buffer (100 mM triethanolamine (TEA), pH=7.0), mixed with 1 g of glass beads and digested for 10 minutes (min) at 4° C. in the globe mill (Retsch). The supernatant (lysate) obtained after 2 min of centrifugation at 12.000 rpm was used in the following activity screening and for determining the enantiomeric excess (ee-value). Ethyl-4-chloroacetoacetate and 2-chloro-1-(3-chlorophenyl)ethane-1-one were used as substrates.

| Batch for activity screening: | |
|---|---|
| 860 µl | 0.1 M $KH_2PO_4/K_2PO_4$ pH = 7.0 1 mM $MgCl_2$ |

-continued

| Batch for activity screening: | | |
|---|---|---|
| 20 µl | NADPH or NADH (10 mM) | |
| 20 µl | lysate | |
| 100 µl | respective substrate (100 mM) | |

The reaction was pursued for 1 min at a wavelength of 340 nm.

| Batch for the determination of the ee-value: | | |
|---|---|---|
| 20 µl | lysate | |
| 100 µl | NADH or NADPH (50 mM) | |
| 60 µl | substrate (ethyl-4-chloroacetoacetate 100 mM) | |

After 24 hours (h), the batches for ee-determination were extracted with chloroform and the enantiomeric excess was determined via gas chromatography (GC).

The enantiomeric excess is calculated as follows:

ee(%)=((R-alcohol−S-alcohol)/(R-alcohol+S-alcohol))×100.

buffer (100 mM triethanolamine, 1 mM $MgCl_2$, pH=7.0) and homogenized by means of a French press.

The crude extract obtained after centrifugation (7000 rpm) was then purified further and reprocessed via FPLC (fast protein liquid chromatography).

The oxidoreductase according to the invention could be purified in two consecutive steps via ion exchange chromatography on Q-Sepharose Fast Flow (Messrs. Pharmacia) and Uno Q (Biorad, Munich, Germany). For this purpose, the lysate obtained after the centrifugation was directly applied to a Q-Sepharose FF-column equilibrated with 50 mM of a potassium phosphate buffer, pH=7.0, and was eluted with an increasing linear salt gradient. In doing so, the oxidoreductase was eluted at 0.2 to 0.3 M NaCl. The oxidoreductase-containing fractions were combined and concentrated to an appropriate volume by means of ultrafiltration (exclusion limit 10 kDa). Subsequently, the fractions of oxidoreductase which had been concentrated were reprocessed and purified further via Uno Q, using the same above-mentioned buffers. The enzyme was thereby eluted at 0.1 M NaCl.

Thereupon, the molecular weight of the purified oxidoreductase obtained was determined via gel permeation (Superdex 200 HR; Pharmacia, 100 mM triethanolamine, pH=7, 0.15 M NaCl).

| | | Ethyl-4-chloroacetoacetate Activity in U/g cells host organism | | | |
|---|---|---|---|---|---|
| DSMZ No. | Name of microorganism | NADH | NADPH | ee-value NADH | ee-value NADPH |
| 1345 | *Yarrowia lipolytika* | 0 | 15 | 70% S | |
| 3434 | *Kluyveromyces thermotolerans* | 0 | 6 | — | — |
| 3435 | *Metschnikowia zobelli* | 0 | 12 | — | — |
| 3795 | *Kluyveromyces lactis* | 0 | 15 | 80% S | 90% S |
| 70130 | *Pichia anomala* | 0 | 9 | 68% S | 90% S |
| 70169 | *Pichia membranefaciens* | 0 | 8 | — | — |
| 70277 | *Pichia angusta* | 13 | 4.5 | racemate | 30% S |
| 70382 | *Pichia pastoris* | 16 | 16 | 64% S | 81% S |
| 70638 | *Candida magnoliae* | 2.5 | 10 | — | 80% R |
| 70125 | *Candida parapsilosis* | 25 | 11 | 52% R | 70% S |
| 2147 | *Pichia methanolica* | 18 | 27 | 84% S | 90% S |
| | *Candida methylica* | 8 | 13 | 94% S | 94% S |
| 70260 | *Pichia capsulata* | 50 | 5 | 100% R | |

DSMZ stands for Deutsche Sammlung für Mikroorganismen und Zellkulturen, Mascheroder Weg 1b, 38124 Braunschweig Definition of enzyme units: 1 U corresponds to the enzyme amount which is required for reacting 1 µmol of substrate per min.

Example 2

Isolation of an NADH-dependent (S)-Specific Oxidoreductase from *Pichia Capsulata*

In order to isolate the NADH-dependent oxidoreductase from *Pichia capsulata* (*P. capsulata*), the microorganism was cultivated as described under Example 1. Upon reaching the stationary phase, the cells were harvested and separated from the medium by centrifugation. The enzyme release was effected by wet grinding using glass beads but may also be achieved by other digestion methods. For this purpose, 100 g of *P. capsulata* were suspended with 400 ml of a digestion Catalase (232 kDa), aldolase (158 kDa), albumin (69.8 kDa) and ovalbumin (49.4 kDa) were used as molecular weight standards.

The following Table 2 summarizes the results obtained.

TABLE 2

| Purification step | Volume [ml] | Activity [U/ml] | Total activity [U] | Specific activity [U/mg] | Yield |
|---|---|---|---|---|---|
| Crude extract | 360 | 2.0 | 752 | 0.07 | 100% |
| Q-Sepharose | 67 | 5.3 | 358 | 5 | 47% |
| Uno Q | 3.5 | 14 | 50 | 41 | 6.6% |

The enzyme activity of oxidoreductase was determined in the test system according to Example 1 (batch activity screening), and the determination of the protein amount was performed according to Lowry et al. *Journal of Biological Chemistry*, 193 (1951): 265-275 or Peterson et al., *Analytical Biochemistry*, 100 (1979): 201-220). The quotient of enzyme activity to protein amount yields the specific activity, wherein the conversion of 1 μmol per min corresponds to 1 unit (U).

The molecular weight of the oxidoreductase according to the invention determined by gel permeation was 140±10 kDa in the native state.

Example 3

Determination of the N-terminal Sequence of the Oxidoreductase According to the Invention After gel permeation, the enzyme preparation according to Example 2 was fractioned in a 10% sodium dodecyl sulfate (SDS) gel and transferred onto a polyvinylidene difluoride membrane (PVDF-membrane).

The conspicuous band at about 35 to 45 kDA was subjected to N-terminal sequencing via Edman degradation (Procise 492 (PE-Biosystems)). The following N-terminal sequence was obtained:

SEQ ID NO: 10          KTQAGYIFKKGA

Example 4

Cloning of Oxidoreductase from *Pichia Capsulata*

The eukaryotic microorganism *Pichia capsulata* belongs to the family of Saccaromycetacea. The genomic structure of said organism exhibits an exon-intron arrangement. Therefore, a cDNA library was prepared from the active cells of *Pichia capsulata* in order to identify the gene sequence which codes for the enantioselective oxidoreductase.

4.1 Preparation of the Total RNA from Cells of *Pichia Capsulata*.

600 mg of fresh cells from *Pichia capsulata* were resuspended in 2.5 ml of an ice-cold LETS (10 mM tris-HCl, pH=7.4, 10 mM EDTA, 100 mM LiCl, 0.2% SDS) buffer. 5 ml (approx. 20 g) of glass beads washed in nitric acid and equilibrated with 3 ml of phenol (pH 7.0) were added to said cell suspension. Thereupon, the entire batch was shaken alternately for 30 seconds (sec) at a time (Vortex Genie 2, Scientific Industries Inc., New York, USA) and cooled on ice for 30 sec and treated for a total period of 10 min. Subsequently, another 5 ml of ice-cold LETS buffer were added. Said cell suspension was centrifuged for 5 min at 11.000 g and at 4° C. The aqueous phase was removed and extracted twice with the same volume of phenol:chloroform:3-methyl-1-butanol (24:24:1). This was followed by an extraction with chloroform. After the final extraction, the total RNA obtained was precipitated for 4 hours at −20° by adding ⅒ vol. of 5 M LiCl.

1 mg of the isolated RNA was used for the m-RNA recovery by means of oligo-dT cellulose (mRNA PrepKit, Qiagen).

After the subsequent precipitation, 5 μg of mRNA were used for the cDNA synthesis (pBluescript IIXR cDNA Library Construction Kit, Stratagene). The library constructed according to the manufacturer's instructions was transformed into XL-10 Gold *E. coli* and examined for (S)-ADH activity.

Two clones (2/1 and 2/2) were identified and isolated on the basis of the extinction decrease with NADH as a cofactor and ethyl-4-chloroacetoacetate as a substrate. Sequencing with Primer T7 (SEQ ID NO: 3) and Primer T3 (SEQ ID NO: 4) via the multiple cloning site of the plasmids contained in the clones resulted in a fragment having a size of 1175 bp (SEQ ID NO: 1). Said fragment codes for a fusion protein comprising 366 amino acids (SEQ ID NO: 2) and consists of the α-fragment of β-galactosidase and the sequence of the oxidoreductase according to the invention.

4.2 Synthesis of a Full-length Transcript Coding for an (S)-ADH from *Pichia Capsulata* Via PCR (Polymerase Chain Reaction)

Based on SEQ ID NO: 1, specific primers were constructed for a subsequent cloning of the full-length transcript into appropriate expression systems. In doing so, 5'-primers having a recognition sequence for Nde I (or Sph I, respectively) and 3'-primers having a recognition sequence for Hind III were modified (SEQ ID NO: 5; SEQ ID NO: 6; SEQ ID NO: 7).

```
Oligo 1-Nde I:
5'-GGAATTCCATATGTCTGCTCTCTCCAAAAC-3'

Oligo 2-Sph I:
5'-CACTGCATGCTGATGTCTGCTCTCTCCAAAAC-3'

Oligo 3-Hind III:
5'-CCCAAGCTTTCATGGAAGCATAACCAATCTT-3'
```

Plasmid DNA isolated from clone 2/1 of the expression library of *Pichia capsulata* served as a template for the polymerase chain reaction. The amplification was carried out in a PCR-buffer [10 mM tris-HCl, (pH 8.0); 50 mM KCl; 10 mM MgSO₄; 1 mM dNTP mixture (N thereby stands for bases A, T, C or G); per 30 pMol of primer and 2.5 U of Platinum Pfx DNA-Polymerase (Invitrogen)] with 50 ng of template and the following temperature cycles:

| Cycle 1: | 94° C., 2 min |
|---|---|
| Cycle 2 × 30: | 94° C., 15 sec |
| | 58° C., 30 sec |
| | 68° C., 75 sec |
| Cycle 3: | 68° C., 7 min |
| | 4° C., ∞ |

After purification, the resulting PCR product was digested via a 1% agarose gel with the aid of endonucleases Nde I and Hind III or endonucleases Sph I and Hind III and was ligated into the backbone of the pET21a vector (Novagen) or the pQE30 vector (Qiagen), which backbone had been treated with the same endonucleases. After transforming 2 il of the ligation batch into *E. coli* Top 10 F' cells (Invitrogen), plasmid DNAs of ampicillin-resistant colonies were tested for the presence of an insert having a size of 1.100 bp by using a restriction analysis with endonucleases Nde I and Hind III or endonucleases Sph I and Hind III. The expression construct pET21-PC#10 was sequenced. The transcript from *Pichia capsulata* coding for the oxidoreductase according to the invention has an open reading frame of, in total, 1026 bp (SEQ ID NO: 8) which corresponds to a protein of 341 amino acids (SEQ ID NO: 9).

4.3 Expression of the Oxidoreductase According to the Invention from *P. Capsulata* in Star BL 21 (De3) *E. Coli* Cells Competent *Escherichia coli* StarBL21 (De3) cells (Invitrogen) were transformed with the expression construct pET21-PC#10 coding for the oxidoreductase according to the invention.

The transformed strain was cultivated in an LB medium (1% tryptone, 0.5% yeast extract, 1% NaCl) with ampicillin (50 ig/ml) until an optical density, measured at 500 nm, of 0.5 was reached. The production of the recombinant oxidoreductase protein was initiated by adding isopropylthiogalactoside (IPTG) at a final concentration of 1 mM. The induction batch was incubated for another 15 h at 25° C. and 220 rpm.

The enzyme activity achieved amounted to approx. 6000 U/g of wet cell mass.

4.4 Expression of the Oxidoreductase According to the Invention from *P. Capsulata* in RB791 *E. Coli* Cells Competent *Escherichia coli* RB791 cells were transformed with the expression construct pQE30-PC#12 coding for the oxidoreductase according to the invention.

The transformed strain was cultivated in an LB medium (1% tryptone, 0.5% yeast extract, 1% NaCl) with ampicillin (50 ig/ml) until an optical density, measured at 500 nm, of 0.5 was reached. The production of the recombinant oxidoreductase protein was initiated by adding IPTG at a final concentration of 0.1 mM. The induction batch was incubated for another 15 hours at 25° C. and 220 rpm. The enzyme activity achieved amounted to approx. 1000 U/g of wet cell mass.

Example 5

Characterization of the Recombinant Oxidoreductase from *P. Capsulata*

5.1 pH Optimum

The buffers indicated in Table 3 were prepared. The concentration of the respective buffer components amounted to 50 mM in each case.

TABLE 3

| pH value | buffer system |
|---|---|
| 4 | Na-acetate/acetic acid |
| 4.5 | Na-acetate/acetic acid |
| 5 | Na-acetate/acetic acid |
| 5.5 | $KH_2PO_4/K_2PO_4$ |
| 6 | $KH_2PO_4/K_2PO_4$ |
| 6.5 | $KH_2PO_4/K_2PO_4$ |
| 7 | $KH_2PO_4/K_2PO_4$ |
| 7.5 | $KH_2PO_4/K_2PO_4$ |
| 8 | $KH_2PO_4/K_2PO_4$ |
| 8.5 | $KH_2PO_4/K_2PO_4$ |
| 9 | glycine/NaOH |
| 9.5 | glycine/NaOH |
| 10 | glycine/NaOH |
| 11 | glycine/NaOH |
| Measuring batch (30° C.): | |
| 870 μl | of each of the buffer systems mentioned in Table 3 |
| 20 μl | NADH 10 mM (8.6 mg/ml water) |
| 10 μl | enzyme diluted |

Incubation lasted for about 2 to 3 min, thereupon 100 μl of a substrate solution (100 mM ethyl-4-chloro-3-oxobutanoate were added.

In order to determine the pH optimum, the enzymatic reaction was determined in the respective buffer indicated in Table 3. In order to determine the pH optimum for the oxidation reaction, NADH was used as a cofactor and (S)-methyl-3-hydroxybutanoate was used as a substrate. For the enzyme according to the invention, a pH optimum of 6.5 to 7 could thereby be determined for the reduction reaction and a pH optimum of 7.8 to 8.2 could be determined for the oxidation reaction.

5.2 pH Stability

The determination of the activity of the recombinant oxidoreductase was examined by storage in the buffer systems mentioned in Table 3. For this purpose, the various buffers (50 mM) were prepared in a pH range of 4 to 11, and the oxidoreductase produced according to Example 4 was diluted therewith. After 30, 60 and 300 min of incubation, 10 μl were removed from the batch and used in the activity test according to Example 1.

Thereby, the initial value is the measured value which was obtained immediately after diluting (1:20) the enzyme in the potassium phosphate buffer 50 mM pH=7.0. Under the given conditions, said value corresponded to an extinction variation of approx. 0.70/min and was set as a 100% value, and all the following measured values were set in relation to said value.

In doing so, it was detected that the recombinant oxidoreductase from *P. capsulata* is stable at a pH of 5.5 to 8.5 and can be incubated for at least 5 h without any substantial loss in activity. Incubations at pH values above 9.0 and below 5.0 resulted in an immediate deactivation of the enzyme.

5.3 Temperature Optimum

In order to determine the optimum test temperature, the enzyme activity was measured in the standard measuring batch in a temperature range of 15° C. to 70° C. As can be seen in Table 4, the enzyme reaches its maximum activity at 45° C., afterwards the activity decreases rapidly.

TABLE 4

| Temperature (° C.) | Activity in U/ml undiluted enzyme |
|---|---|
| 15 | 73 |
| 20 | 83 |
| 25 | 128 |
| 30 | 135 |
| 35 | 163 |
| 40 | 170 |
| 45 | 176 |
| 50 | 122 |
| 55 | 45 |
| 60 | 0 |
| 65 | 0 |
| 70 | 0 |

5.4 Temperature Stability

The temperature stability was determined for the range of 15° C. to 70° C. in a manner analogous to that described under Example 5.2. For this purpose, a 1:20 dilution of the purified oxidoreductase was incubated in each case for 60 min and for 180 min at the respective temperature and was measured subsequently at 30° C. with the above-mentioned test batch. Also in this case, the measured value obtained immediately after diluting the purified oxidoreductase in a potassium phosphate buffer 50 mM pH=7.0 was used as the initial value. Said value was set as a 100% value also in this example.

Here, the enzyme is completely stable in a temperature range of 15° C. to 40° C. and does not show any loss in activity after 3 h of incubation. At 55° C., an enzyme activity can no longer be detected already after 30 min.

5.5 Substrate Spectrum/enantiomeric Excess

The substrate spectrum of the oxidoreductase according to the invention was determined by measuring the enzyme activity with a number of ketones, oxoacids and esters thereof. For this purpose, the standard measuring batch according to Example 5.1 was used with different substrates. The activity with ethyl-4-chloroacetoacetate was equalled to 100% and all the other substrates were set in relation thereto.

For the determination of the ee-value, the following reaction batch was used for selected substrates.

| 100 μl | NADH (50 mM) |
|---|---|
| 60 μl | substrate (100 mM) |

+1 to 2 U of the oxidoreductase according to the invention

The batches for ee-determination were extracted with chloroform after 24 h and the enantiomeric excess of the resulting alcohol was determined via GC.

TABLE 5

| Substrate | Relative activity % | Stereo-selectivity |
|---|---|---|
| Ketones | | |
| 1-Phenyl-2-propanone | 24 | 97% S |
| 2-Chloro-1-(3-chloro-phenyl)ethane-1-one | 21 | 100% R |
| Acetophenone | 4 | n.d. |
| Caprylophenone | 0 | n.d. |
| 2-Octanone | 88 | 100% S |
| 3-Octanone | 30 | n.d. |
| 2-Butanone | 99 | 50% S |
| 4-Hydroxy-2-butanone | 99 | 90% S |
| Ethyl-2-oxovaleriate | 41 | 97% S |
| Ethyl-2-oxo-4-phenylbutanoic acid | 76 | 95% S |
| Ethyl pyruvate | 10 | 100% S |
| Ethyl phenyl glyoxylate | 5.2 | 100% R |
| 3-Oxoacid ester | | |
| Ethyl-4-chloroacetoacetate | 100 | 99% R |
| Methyl acetoacetate | 150 | 97% S |
| Ethyl-8-chloro-6-oxooctanoic acid | 20 | 100% R |
| Dimethyl-3-oxo-1,8-octandioic acid | 3.5 | n.d. |
| Ethyl-3 oxovaleriate | 67 | n.d. |
| Ethyl acetoacetate | 100 | 99% S |
| 2-Oxovaleric acid | 0 | n.d. |
| 2-Oxo-3-phenyl propionic acid | 0 | n.d. |
| 2-Oxobutanoic acid | 0 | n.d. | n.d. means not determined

As can be seen in Table 5, a broad spectrum of 2- and 3-oxoacid esters as well as aromatic and aliphatic ketones are stereoselectively reduced from the oxidoreductase according to the invention.

5.5 Solvent Stability

The enzyme stability of the oxidoreductase from *P. capsulata* was examined in the presence of organic solvents. For this purpose, the oxidoreductase was in each case diluted 1:20 with the indicated solvent mixtures (in case of water-miscible organic solvents) and was incubated at room temperature (20° C. to 24° C.; RT). Subsequently, 10 μl of the enzyme solution were used in the standard test batch. Also in this case, the initial value was equalled to 100% after dilution in the buffer (potassium phosphate buffer (KPP) 100 mM, pH=7.0), and all the other values were set in relation to said initial value.

In case of water-immiscible organic solvents, the dilution likewise took place in a potassium phosphate buffer, the same volume of an organic solvent was added to the batch and the batch was incubated at RT in a thermomixer at 170 rpm. The activity was measured from the aqueous phase. Table 6 shows the results.

TABLE 6

| Activity | 8 h | 24 h |
|---|---|---|
| Buffer KPP 100 mM pH = 7 1 mM MgCl$_2$ | 100% | 100% |
| 5% isopropanol | 77% | 77% |
| 10% isopropanol | 72% | 72% |
| 20% isopropanol | 46% | 46% |
| 30% isopropanol | 18% | 18% |
| 5% EtOH | 77% | 77% |
| 10% EtOH | 77% | 77% |
| 20% EtOH | 100% | 100% |
| 30% EtOH | 64% | 64% |
| 10% DSMO | 42% | 45% |
| 20% DSMO | 30% | 30% |
| ethyl acetate | 2 | 0 |
| butyl acetate | 53% | 28% |
| diethyl ether | 100% | 100% |
| methyl tert-butyl ether | 100% | 100% |
| diisopropyl ether | 100% | 100% |
| chloroform | 51% | 0% |
| hexane | 60% | 20% |
| heptane | 74% | 43% |
| cyclohexane | 85% | 70% |

EtOH stands for ethanol;
DSMO stands for dimethyl sulfoxide

As can be seen in Table 6, the oxidoreductase from *P. capsulata* displays a surprising stability towards organic solvents. In contrast to the established doctrine, the oxidoreductase according to the invention is even stabilized in organic water-miscible and water-immiscible solvents, compared to an incubation in the pure buffer. Thus, the oxidoreductase according to the invention can be used in a two-phase system as described in DE 101 19274 A1.

5.7 Preparative Conversions 5.7.1 Reduction of ethyl-4-chloroacetoacetate to ethyl-(R)-4-chloro-3-hydroxybutanoate For the preparative batch, a mixture of 34 1 of a buffer (100 mM TEA, pH=7, 1 mM ZnCl$_2$, 10% glycerol), 4 1 isopropanol, 4 1 4-chloroacetoacetate, 4 g NAD and 3.6 million U of recombinant oxidoreductase from *Pichia capsulata* was incubated for 24 h at room temperature under constant mixing. After 24 h, 99% of the 4-chloroacetoacetate used was reduced. Subsequently, the reaction mixture was extracted with ethyl acetate, the solvent was removed by means of a rotary evaporator and the raw product was distilled. In this manner, 2.8 l (3.4 kg) of ethyl-(R)-4-chloro-3-hydroxybutanoate with an enantiomeric excess of 99% were recovered. This corresponds to a yield of 70%, based on the amount of educt used.

5.7.2 Reduction of 2-chloro-1-(3-chlorophenyl)ethane-1-One to (R)-2-chloro-1-(3-chlorophenyl)ethane-1-ol For the preparative batch, a mixture of 164 ml of a buffer (100 mM TEA, pH=7, 1 mM ZnCl$_2$, 20% glycerol), 16 ml isopropanol, 20 g 2-chloro-1-(3-chlorophenyl)ethane-1-one dissolved in 20 ml methyl tert-butyl ether (MTBE), 10 mg NAD and 20,000 U of recombinant oxidoreductase from *Pichia capsulata* was incubated for 24 h at room temperature under constant mixing. After 24 h, 96% of the 2-chloro-1-(3-chlorophenyl)ethane-1-one used was reduced. Subsequently, the reaction mixture was extracted with ethyl acetate, and the solvent was removed using the rotary evaporator. In this manner, 15 g of (R)-2-chloro-1-(3-chlorophenyl)ethane-1-ol with an enantiomeric excess of 100% were recovered. This corresponds to a yield of 77%, based on the amount of educt used.

The invention claimed is:

1. An isolated oxidoreductase comprising the amino acid sequence of SEQ ID NO: 9 and having the enzymatic activity for catalyzing the reduction of a carbonyl compound to the corresponding (S)-hydroxy compound in the presence of NADH and water.

2. An isolated oxidoreductase encoded by a nucleic acid that hybridizes to SEQ ID NO: 8 or its fully complementary strand under stringent conditions comprising washing with 0.1-2.0×SSC solution at 65° C., said oxidoreductase having the enzymatic activity for catalyzing the reduction of a carbonyl compound to the corresponding (S)-hydroxy compound in the presence of NADH and water.

3. The isolated oxidoreductase according to claim 2, comprising an amino acid sequence having more than 90% homology with the amino acid sequence of SEQ ID NO: 9.

4. The isolated oxidoreductase according to claim 1 or claim 2, wherein it is obtainable from yeasts of the genuses *Pichia* or *Candida*.

5. The isolated oxidoreductase according to claim 1, wherein it has at least 99% homology to the amino acid sequence of SEQ ID NO: 9.

6. The isolated oxidoreductase according to claim 1, wherein it is conjugated to one, two, three, four or five water-soluble polymer molecules of a water-soluble polymer.

7. The isolated oxidoreductase according claim 6, wherein the water-soluble polymer is polyethylene glycol.

* * * * *